United States Patent [19]

Bokros

[11] 4,421,507
[45] Dec. 20, 1983

[54] PLUG-TYPE FLUID ACCESS DEVICES

[75] Inventor: Jack C. Bokros, Austin, Tex.

[73] Assignee: Carbomedics, Inc., Austin, Tex.

[21] Appl. No.: 324,040

[22] Filed: Nov. 23, 1981

Related U.S. Application Data

[63] Continuation-in-part of Ser. No. 220,101, Dec. 24, 1980, abandoned.

[51] Int. Cl.³ ............................................. A61M 5/00
[52] U.S. Cl. ..................................... 604/52; 604/175
[58] Field of Search ................. 128/214 R, 274, 348, 128/350; 604/52, 175, 29

[56] References Cited

U.S. PATENT DOCUMENTS

| | | | |
|---|---|---|---|
| 3,765,032 | 10/1973 | Palma | 128/214 R |
| 3,826,257 | 7/1974 | Buselmeier | 128/214 R |
| 3,998,222 | 12/1976 | Shihata | 128/214 R |
| 4,015,601 | 4/1977 | Bokros et al. | 128/214 R |
| 4,108,173 | 8/1978 | Slivenko et al. | 128/214 R |
| 4,108,174 | 8/1978 | Slivenko | 128/214 R |
| 4,164,221 | 8/1979 | Bentley et al. | 128/214 R |
| 4,349,021 | 9/1982 | Raible | 128/214 R |

Primary Examiner—Stephen C. Pellegrino
Attorney, Agent, or Firm—Fitch, Even, Tabin & Flannery

[57] ABSTRACT

Access to internal regions of a living body is achieved by a device, a movable plug and an adaptor. An access tube insertable in a living body is appropriately anchored within the body. The access tube extends above the skin and provides a first passageway for body fluids which is blocked by the movable plug. The adaptor, when linked to the access device, provides a second passageway which allows relocation of the plug to a fluid access position whereat communication is established between the conduit and an external outlet of the adaptor.

20 Claims, 9 Drawing Figures

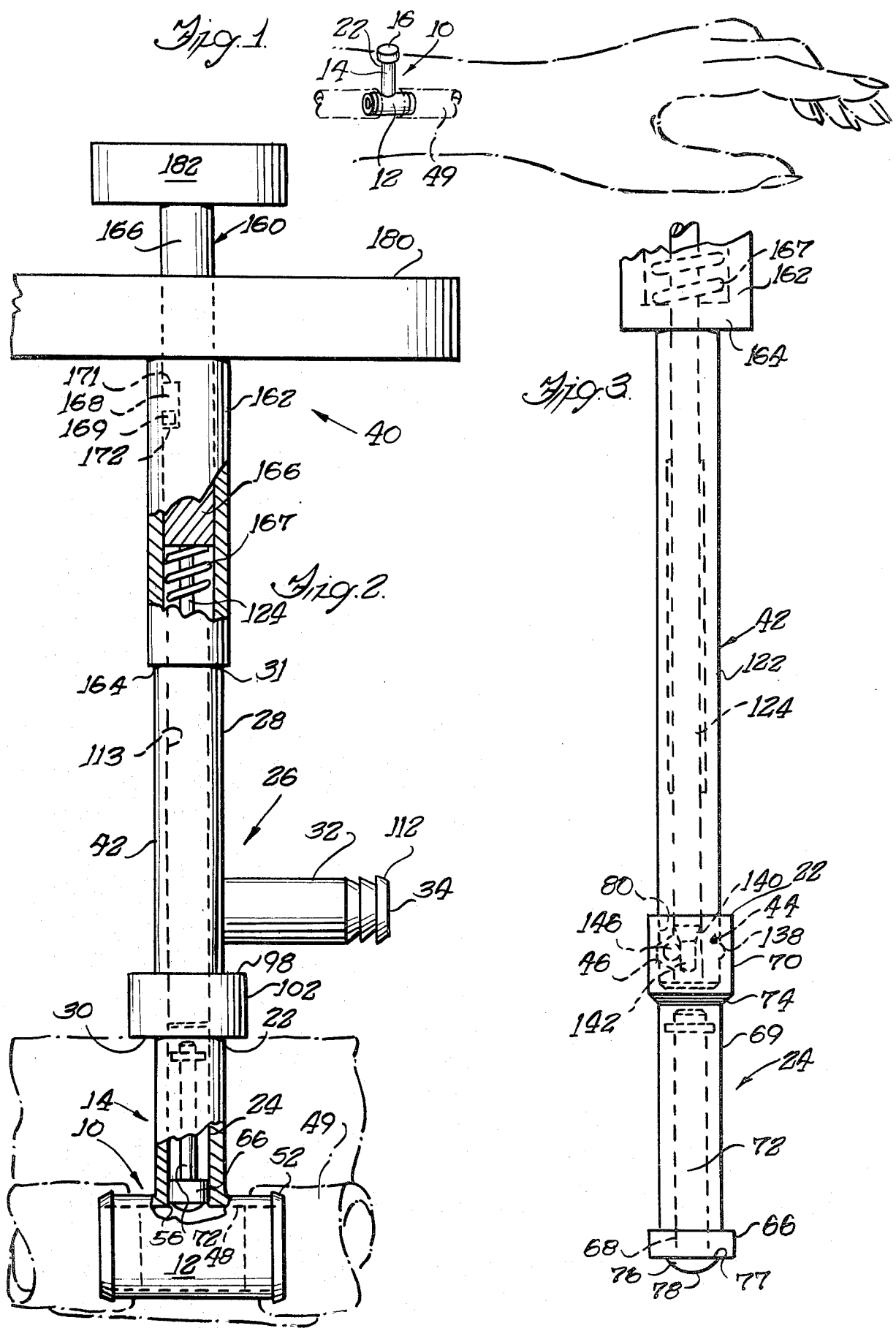

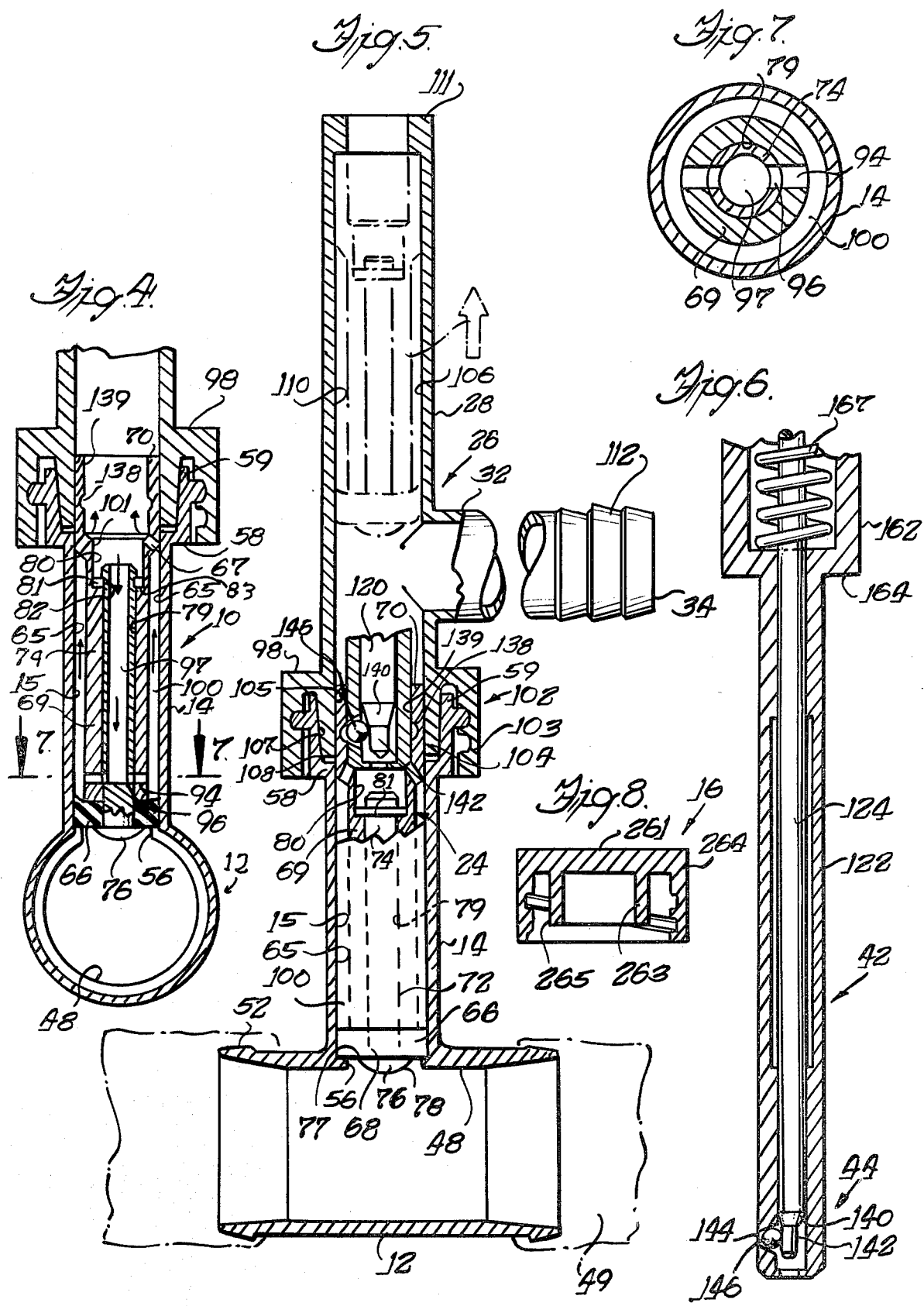

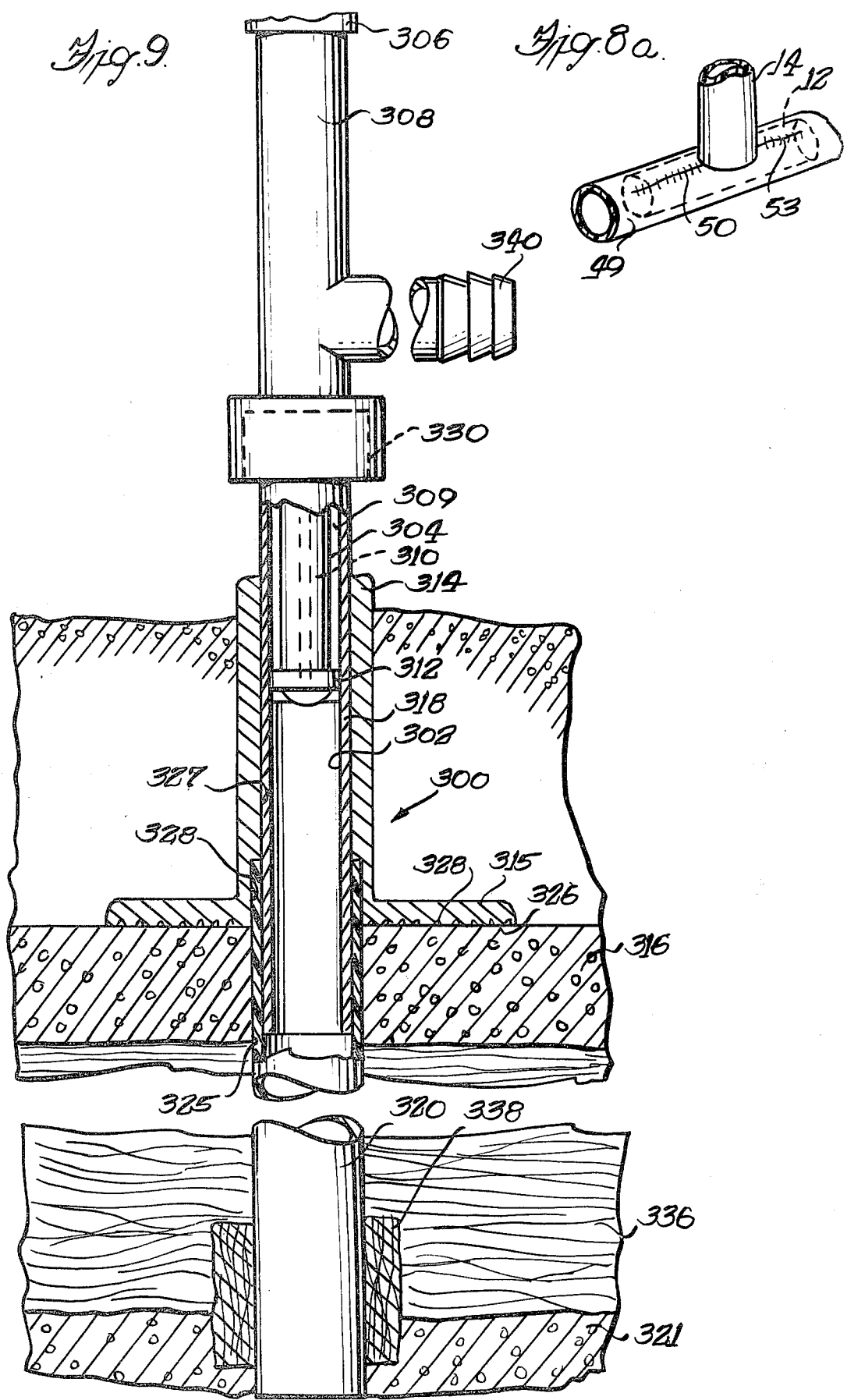

PLUG-TYPE FLUID ACCESS DEVICES

This application is a continuation-in-part of U.S. patent application Ser. No. 220,101 filed Dec. 24, 1980, now abandoned. This invention relates to medical devices and more particularly to improvements in such devices that provide access to internal regions of the living body.

BACKGROUND OF THE INVENTION

There is a need for devices to provide access to internal regions of a living body, such as the circulatory system or body cavities in circumstances requiring, for example, repeated withdrawal of blood, peritoneal dialysis or injections of drugs, which may be continuous or repeated, into a patient.

While access to the circulatory system is ordinarily gained by use of a needle and syringe, repeated injections may cause scarring and eventual collapse of the vein or infection. Therefore, when repeated injections or blood withdrawals are required, a percutaneous access device is implanted through which access may be gained to the circulatory system and thereafter closed off.

A number of designs for blood access devices have been developed, many of which use a valve which opens and closes to control access to the circulatory system. Problems have developed with such devices because blood may seep into the valve mechanism, causing the valve to stick. Such sticking is especially troublesome because a surgically implanted device is not easily accessible for repairs. Furthermore, blood which has seeped into the valve mechanism is a breeding ground for bacteria which may cause infection in the patient, and stagnant blood or denatured protein in the valve mechanism can cause clotting.

A blood access device is described in U.S. Pat. No. 4,164,221 in which a blood passageway connecting a blood vessel with the outside of the body is blocked by a frustoconical plug. When a valve chamber, including a blood outlet, is secured to the outer end of the passageway, and when a reciprocable stem member is connected to the outer end of the plug, a pull on the stem member relocates the plug to where it allows blood to flow through an annular region in the valve chamber along the plug into the blood outlet at the outer end of the valve chamber. The frustoconical plug has a large area of surface contact with the passageway, and when the displaced plug is reinserted into the passageway, blood is trapped between the periphery of the plug and the passageway. Even when the plug of the device described in the U.S. Pat. No. 4,164,221 patent is pulled fully outward, it is centrally located in the blood passageway and chamber and tends to obstruct the free flow of blood from the blood vessel to the blood outlet.

All blood access devices are inconvenient and unsightly, and for cosmetic reasons, a blood access device should be as small as possible. Obtaining a maximum amount of blood through a small device requires that the passageway leading externally be as large as possible for the size device implanted.

A blood access device for permanent implantation in the human body must also be biocompatible with body tissue to prevent rejection reactions and associated infection. Surfaces which interface with blood should be thromboresistant to prevent blood clotting.

For several medical applications it is desirable to have continual access to body cavities, and in particular to the peritoneum. Access to the peritoneum is required for peritoneal kidney dialysis, which involves pumping a large volume, e.g., about a gallon, of dialysis fluid into the peritoneum and withdrawing the fluid after a period of time during which dialysis is effected. It is well known that certain drugs are more effective if administered peritoneally rather than interveneously, and if a drug such as insulin is to be administered on a continuous basis, an accesssing device will obviate repeated painful administration through the abdomen.

Because of the considerable expense involved in both inpatient and outpatient care, attempts are made wherever possible to supply patients requiring repeated treatment with support equipment by which they alone, or with the aid of relatively untrained persons, may treat themselves. For example, persons requiring repeated doses of insulin are taught to treat themselves. There is also a movement toward home dialysis in order to alleviate the enormous expenses incurred at dialysis centers. Devices which permit self-treatment should be easy to operate and as foolproof as possible. Provisions need also be made for the patient to maintain sterility of internal access devices.

Any internal access device should, of course, cause as little pain and inconvenience to the patient as possible. Thus an access device should be designed for insertion in a manner which will prevent dislodgement of the device by normal activity of the patient.

SUMMARY OF THE INVENTION

An internal access device includes a tubular conduit insertable in a living body providing access to body fluids through an open end which extends externally of the body and means to anchor the device within the body. A plug is inserted in the access tube to close off fluid communication between the conduit and the exposed end. An adaptor with an interior diameter substantially identical to that of the access tube attaches to the exposed end thereof. An extractor is used to engage the plug and pull it from the access tube to a position in the access tube whereat communication is established between the conduit and an outlet tube of the adaptor which leads externally.

BRIEF DESCRIPTION OF THE DRAWINGS

FIG. 1 is a perspective view of a blood access device depicting how it might be inserted in the circulatory system of a living body;

FIG. 2 is an enlarged elevation view of a combination of the blood access device of FIG. 1 with an adaptor and extractor;

FIG. 3 is a fragmentary elevation view of the extractor of FIG. 2 shown engaged with the plug;

FIG. 4 is an enlarged fragmentary sectional view taken generally along the line 4—4 of FIG. 2 of the adaptor linked to the plug-containing blood access device;

FIG. 5 is a sectional view taken generally along the line 5—5 of FIG. 4 illustrating withdrawal movement of the plug to an upper position within the adaptor;

FIG. 6 is a sectional view of the lower end of the extractor taken along lines 6—6 of FIG. 3;

FIG. 7 is an enlarged sectional view taken along line 7—7 of FIG. 4;

FIG. 8 is a cross-sectional view of the cap shown in FIG. 1;

FIG. 8a is a perspective view illustrating an alternative insertion of the blood access device into a blood vessel; and FIG. 9 is an elevation view, partially cut away and partially in section, of an alternative embodiment of an access device adapted to provide access to the peritoneum.

DETAILED DESCRIPTION OF THE PREFERRED EMBODIMENTS

FIG. 1 illustrates a blood access device 10 including a tubular conduit 12 which has been inserted into the circulatory system of the living body and an access tube 14 which is integral with the conduit 12 and extends above the skin to provide a first blood passageway 15 (FIG. 5). The blood access device 10 is sealed by a cap 16.

The conduit 12 is in fluid communication with the access tube 14. Blood flow through the first passageway 15 to the exposed end 22 of the access tube 14 is blocked by a removable plug 24.

When blood access is desired, the cap 16 is removed from the access device 10 and an adaptor 26 (FIGS. 2 and 5) is fitted on to the exposed end 22 of the blood access device 10 to communicate therewith. The adaptor 26 consists of a main tube 28 with a lower end 30 attachable to the access tube 14, an open upper end 31 and a blood outlet or side tube 32 having an open end 34 for communication with external devices. (To aid description, "lower" is herein used to denote the direction toward the interior of the body and "upper" is used to describe the direction toward the exterior of the body).

An extractor 40 (FIGS. 2, 3 and 6) is provided that contains a small diameter lower gripping portion 42 which may be inserted into the upper end 31 of the adaptor 26 and through the entire length of the main tube 28 so that a latching means 44 may reversibly engage with a cooperating latching member 46 at the top of the plug 24. When the plug 24 is engaged with the extractor 40, the plug 24 may be pulled from the access tube 14 through the adaptor 26 to a blood access position above the side tube 32 establishing communication between the conduit 12 and the side tube 32, so that blood may flow from a blood vessel to an external device attached to the side tube 32.

As an aid to understanding the invention, the blood access device 10, plug 24, adaptor 26 and extractor 40 will now be described in greater detail.

The conduit 12 of the blood access device 10 (FIGS. 4 and 5) is generally cylindrical in shape with a smooth cylindrical central passageway 48 for unhindered blood flow. As one means of inserting the access device (FIG. 1) in a blood vessel, the blood vessel is severed and the severed ends 49 are attached at each end of the conduit 12 by conventional means, such as by suturing. Ridges 52 on the exterior of the conduit 12 provide for a more secure union between the blood vessel ends 49 and the conduit 12. As another means of inserting the access device in a blood vessel (FIG. 8a), the blood vessel 49 is opened with a longitudinal slit 50, the conduit 12 inserted through the slit and the slit closed around the access tube 14 by sutures 53. Alternatively, the device may be incorporated in a vascular graft formed of woven or non-woven fabric, e.g., non-woven fabric sold under the trade name Gore-tex. Such a graft may be used as a shunt between a blood vessel and an artery.

The access tube 14 communicates with the conduit 12 through an orifice 56 which has a diameter slightly less than the interior diameter of the access tube 14 preventing the plug 24 from being pushed downward into the conduit 12 yet providing ample passageway for blood when the plug 24 is removed.

An annular male threaded member 59 for linking the blood access device 10 either to the adaptor 26 or to the cap 16 extends from the upper end of the access tube 14. The threaded member 59 has an interior diameter larger than the access tube 14, for reasons which will be clarified hereinafter, and is integrally joined to the access tube 14 by an annular shoulder 58.

The plug 24 slides upward and downward within the access tube and the adaptor 26. At the lower end of the plug 24 a resilient annular sealing member 66 blocks blood flow therearound. The sealing member 66 has an outer diameter substantially equal to or slightly larger than the interior diameter of the access tube 14 so that the sealing member 66 abuts the interior wall 65 of the access tube and seals therewith. A bore 68 through the sealing member facilitates its attachment to the body of the plug 24, as hereinafter described.

The body of the plug 24 comprises a narrow tubular portion 69 which abuts the sealing member 66 at the lower end and terminates at the upper end in a larger tubular portion 70 of diameter substantially equal to the interior diameter of the access tube 14. A frustoconical shoulder 67 integrally connects the narrow and larger tubular portions 69 and 70 of the plug 24. The distance between the front of the sealing member 66 and the top of the frustoconical shoulder 67 is slightly shorter than the first passageway 15 so that when the plug 24 is fully inserted in the access tube 14, the larger tubular section 70 of the plug 24 extends slightly into the access tube 14 to provide lateral stability of the plug within the passageway 15.

A connector 72, consisting of an upper pipe 74 which terminates in a lower head 76, secures the sealing member 66 to the body of the plug 24. The connector head 76 which is larger in diameter than both the pipe 74 and the bore 68 through the annular sealing member 66 has an upper flat side 77 from which the pipe 74 extends and a lower rounded side 78. The pipe 74 with an exterior diameter substantially equal to the interior diameter of the narrow tubular portion 69 of the plug 24, extends from the head 76, through the bore 68 in the sealing member 66, through the bore 79 of the narrow tubular portion 69, and into an enlarged-in-diameter portion 80 thereof where a snap ring 81 is located in an annular groove 82 in the end of the pipe 74. The annular groove 82 is appropriately spaced from the head 76 so that, when the snap ring 81 is in place, it abuts the lower end 83 of the enlarged portion 80, and the flat side 77 of the connector head 76 abuts the lower surface of the sealing member 66 and blocks fluid passage through the bore 68.

Channel means are provided so that surfaces of the plug 24 and surfaces of the access tube 14 above the sealing member 66, which may become coated with blood, may be cleaned by flushing when the plug is located in a blocking position in the access tube 10. Openings in the wall of pipe 74 are aligned with openings 94 in the narrow tubular portion 69 of the plug 24. The openings 94 and 96 provide communication between the center channel 97 of the pipe 74 with an annular vacant region 100 between the narrow tubular portion 69 of the plug 24 and the interior wall 65 of the access tube 14. A pair of orifices 101 are provided in the frustoconical shoulder 67 to provide communication between the annular region 100 and the interior of the larger tubular portion 70.

To clean surfaces of the plug and surfaces of the blood access tube 14 above the sealing member 66, cleaning solution is injected into the center channel 97 of the pipe 24 after the plug has been returned to the blocking position. The solution flows through the openings 94 and 96, upward in the annular region 100 and out through the orifices 101 in the frusto conical shoulder 67.

Integrally connected with the lower end of the main tube 28 of the adaptor 26 by an annular shoulder 98 is a linking means 102 comprised of a female threaded member 103 which cooperates with the male threaded member 59 of the access tube 14 to join the adaptor 26 to the access tube 14. Concentric with the female threaded member is a smaller-in-diameter annular skirt 104 having an interior wall 105 which is a continuation of the interior wall 106 of the main tube 28 of the adaptor 26. The exterior wall 107 of the skirt 104 and interior wall 108 of the male member 59 are frustoconical, being of greater diameter at their respective upper ends. When the male and female members are engaged, (FIG. 5) the skirt 104 of the adaptor 24 extends generally to the shoulder 58 of the access device 10, and the outer and inner frustoconical walls 107, 108 abut to form a fluid-tight seal. The second passageway 110 provided by the main tube 28 of the adaptor 26 coaxially aligns with the first passageway 15 of the access device 10 to form a continuous passageway of substantially uniform diameter through which the plug 24 may be relocated with the sealing member 66 at all times preventing fluid flow therearound.

The main tube 28 of the adaptor 26 extends sufficiently above the side tube 32 providing a chamber portion 113 to receive the plug 24 when it is withdrawn from its blocking position within the access tube. When the plug 24 is fully withdrawn into the chamber portion 113, the sealing member 66 is above the side tube 32 to allow fluid to flow from the conduit 12 out through the side tube. While the upper end of the main tube 28 is open, an annular ring 111 integral with the interior wall 106 of the adaptor extends inward therefrom to limit upward movement of the plug 24 so that the plug may not accidentally be pulled from the open upper end of the adaptor.

The exterior of the side arm 32 preferably has ridges 112 for securely retaining flexible tubing (not shown). The interior diameter of the side arm 32 is preferrably generally equal to the interior diameter of the main tube 28 to permit maximum blood flow therethrough.

Suitable means, such as threads, a bayonet fitting or hooks are employed to latch the extractor 40 to the upper end of the plug 24. In the illustrated embodiment as best seen in FIG. 5, the latching means 44 of the extractor 40 comprises a ball lock which reversibly engages the cooperating latching member 46 in the form of an annular groove 138 in the interior wall 139 of the wider tubular portion 70 of the plug 24. The ball lock, which allows for quick gripping and quick releasing of the plug 24 by the extractor 40, is included near the lower end of the extractor. The gripping portion 42 fits through the upper open end 31 of the adaptor 26 to grip the plug 24 after the adaptor 26 has been joined to the access device 10 and includes a tubular lower section 122 wherein a rod 124 is slidably disposed. The lower end of the rod 124 is necked down to form a frustoconical camming surface 140 and terminates in a narrow tip 142. A hollow 144 is formed in the sidewall of the tube 122 which holds a ball 146 of diameter slightly greater than the dimension of the exterior entrance to the hollow 144. When the gripping portion 42 of the extractor 40 is fully inserted into the adaptor 26 so that a shoulder 164 of the extractor abuts the upper end 31 of the adaptor, the hollow 144 aligns with the annular groove 138 in the interior wall 139 of the wider tubular portion 70 of the adaptor 26. When the rod 124 is slid downward, the ball 146 is cammed outward by the camming surface 140 until it is locked in this outward position by the surface of the rod 124 with the ball 146 extending partially through the entrance of the hollow 144 and into the annular groove 130 in the plug 24 with which it is thus mated.

The ball lock is activated by a plunger mechanism 160 in which a plunger 166 is biased outward of a plunger body 162 into a non-actuating position by a helical spring 167 and which may be displaced to an actuating positon by depression of the plunger. Depression of the plunger 166, which is accomplished by gripping a handle portion 180 of the plunger body while pushing downward a knob portion 182 at the upper end of the plunger, slides the rod 124, to which the plunger is integrally connected, downward through the lower tubular section 122. The upward or non-actuating position and the lower or non-actuating positions of the plunger 166 are defined by the lower and upper walls 171, 172 of a vertical plunger slot 168 abutting a boss 169 extending inward of the plunger body 162.

After screwing the adaptor 26 to the access device 10 and connecting the side tube 32 of the adaptor to an external device, the user inserts the extractor 40 until the shoulder 164 of the extractor abuts the upper end 31 of the adaptor. The user depresses the plunger 160 to activate the ball lock to grip the plug 24. While keeping the plunger 160 depressed, the user pulls the extractor 40 upward until the plug 24 abuts the annular ring 111 at the upper end 31 of the adaptor 26. With the plug in the withdrawn position at which the sealing member 66 is located outward of the side tube 32, blood flows from the conduit 12 through the side tube. The plunger 160 is thereafter released, unlocking the ball 146, and the extractor 40 is removed. The pressure of the sealing member 66 against the interior wall 106 of the adaptor 26 maintains the plug 24 in its withdrawn position until it is pushed inward. When it is desired to close off blood flow, the extractor 40 is reinserted, the plunger 160 is depressed and the plug 24 is pushed fully down into the blocking position within the access tube 14 to reseal the first passageway 15. The adaptor 26 is unscrewed, and the access device 10 is washed and recapped.

The cap 16 is applied to the blood access device in a manner identical to application of the adaptor 26. The cap 16 has a circular top 261 with a threaded outer skirt 264 and a concentric inner skirt 263 depending therefrom. The inner skirt has a frustoconical exterior surface 265 to seal with the frustoconical interior 108 surface of the male member 59 of the access device 10 so that a disinfectant solution may be contained therein between times when blood access is desired.

The blood access device 10 is designed for generally permanent implantation in the human body and is strong and durable. The surfaces should be biocompatible and thromboresistant. The device 10 may be made of metals, e.g., titanium, stainless steel and chromium-cobalt alloys, such as those sold under the trade name Vitallium. The sealing member 66 of the plug 24 is made of resilient material, such as silicone rubber.

The remaining components may be made of any suitably strong and durable material provided that surfaces which contact blood are thromboresistant. Surfaces may be made biocompatible and thromboresistant by coating them with carbon, i.e., by vapor deposition as described in U.S. Pat. No. 3,952,336 issued Apr. 27, 1976 to Bokros, et al.

Several advantages of the blood access device should now become apparent. The blood passageway includes the entire interior diameter of the housing 10, a feature not available in valve type blood access devices. This diameter is continued through the second passageway 110 of the adaptor 26 and through the side tube 32 so that a maximum blood flow is obtained from a small blood access device.

There are not valves or moving parts in the housing to stick or malfunction which would require a surgical procedure to remove the blood access device 10 from the body. Likewise, the plug 24 which sits in the access tube 14 has no moving parts, and should any part of the plug 24 show signs of wearing out, the plug itself could be easily replaced simply by applying a tourniquet to the arm to prevent significant loss of blood, quickly pulling out the old plug and inserting a new one. The adaptor 26 and extractor 40, being devices external to the body, can be replaced or repaired at will. All surfaces of the blood access device 10 and plug 24, which contact blood and are disposed above the sealing member 66, are easily washable, and a disinfectant solution may be sealed in the access tube 14 by the cap 16 to prevent bacterial growth and possible infection. Furthermore, the sealing member 66 rubs against the inner surface of the passage 15 as the plug 24 is inserted and extracted, thereby wiping the inner surface to help keep it clean.

Illustrated in FIG. 9 is an assembly including an internal access device 300 adapted for insertion into a living body to provide communication to a fluid-containing body cavity, in particular the peritoneum, through the rib cage rather than directly through the abdomen. Access through the rib cage permits anchoring of the device to one of the rib bones and passage of the device through the relatively stationary soft tissue overlying the ribs rather than through the continually moving soft tissue covering the abdomen to permit greater activity of the patient without risk of dislodging the device.

The internal access device 300 provides a passageway 302 to the peritoneum, and a plug 304 closes the outer end of the passageway. An extraction device 306 is used to withdraw the plug from the passageway into an adaptor 308 that connects the peritoneum passageway to appropriate external apparatus. The extractor 306 and the "T" shaped adaptor 308 are substantially as described hereinabove in reference to the blood access device, with appropriate adjustment in size to provide for an appropriate passageway as required for peritoneal access devices. The plug 304 likewise is similar to that described hereinabove in reference to the blood access device providing a surrounding vacant region 309 within the passageway 302 and having a fluid passageway network 310 above a sealing member 312 to permit cleaning of surfaces of the plug and passageway.

The access device 300 includes the access tube 318 and an outer sleeve 314 having an inner flange portion 315 by which the device is anchored to a rib bone 316. The sleeve 314 is proportioned to extend above the skin when the flange 315 is anchored to the bone. The sleeve is preferably formed of graphite coated with pyrolytic carbon, such as that sold under the tradename Pyrolite. The sleeve may also be formed of a metal, such as titanium which is compatible with body tissues; the surfaces which contact soft tissue are preferably coated with pyrolytic carbon. Alternatively, the surfaces which contact soft tissues may be covered with a fabric layer which promotes the ingrowth of tissue and possibly coated with vapor-deposited carbon, such as that sold under the tradename Biolite. The flange 315, which typically has a diameter between about two and about three times the outside diameter of the outer portions of the sleeve 314, has a bone contact surface 326 formed with indentations or pores 328, and a cement containing hydroxyapatite (HA) or an HA coating can be used to attach the porous surface to the bone.

The rigid access tube 318, which receive the plug 304, is held in a bore 326 which extends through the sleeve 314. The tube 318 is held in the bore with an adhesive, or alternatively, the sleeve 314 is shrink-fitted around the rigid tube. The outer end of the access tube 318 extends above the upper end of the sleeve 314 and has a male fitting 330, substantially as described hereinabove in reference to the blood access device, for alternate attachment to the adaptor 308 or a covering cap (not shown). The opposite end of the access tube 318 extends inward of the flange 315 and substantially through a circular opening 325 surgically formed in the rib bone 316.

The flexible tube 320, which extends from the rib bone 316 to the peritoneum 321, is formed of a biocompatible polymeric material, such as silicone rubber or polyurethane. Its outside diameter is matched to that of an enlarged-in-diameter inner portion 328 of the sleeve bore 327 while its inside diameter is matched to outside diameter of the access tube 318. At its outer end, the flexible tube extends through the bore in the bone, around the lower end of the rigid tube 318 and is received in an annular area 334 of the enlarged-in-diameter bore portion 328 around the rigid tube. The outer end of the flexible tube 320 is adhesive-bonded or heat-bonded to the sleeve 314 and access tube 318 assuring permanent attachment thereto. The inner end of the flexible tube is open and extends through the peritoneum wall 336.

To maintain the integrity of the peritoneal cavity, the flexible tube carries a cuff 338 for suturing to an opening surgically formed in the peritoneum wall. Preferably the cuff 338 is formed of dacron velour or another open weave fabric which promotes ingrowth of tissue into the fabric, and the fabric is preferably coated with vapor-deposited carbon giving the cuff excellent biocompatible properties.

The members of the access device 300 are preassembled to facilitate insertion during a surgical procedure. To implant the device, the bore 325 is formed in a lower rib, the inner end of the flexible tube 320 extended into the peritoneum, the cuff 338 sutured the peritonial wall and the flange 315 anchored to the rib bone.

With the access device in place, periodic access to the peritoneal cavity is achieved by attachment of the adaptor 308, connection of the adaptor to an external device through the side tube 340 of the adaptor and withdrawal of the plug 304 from the rigid tube 318 by the extractor 306. After the plug is reinserted in the passageway 320 to close off access to the peritoneum, the outside surfaces of the plug and interior surfaces of the access device are washed by an appropriate cleaning fluid.

The implanted access device 300 is carried without sigificant irritation to the user as the rib bone and overlying tissue are generally stationary relative to each other during normal activities. The flexible tubing, which bypasses the diaphragm, is substantially unfelt in place. The access device is implanted in a part of the body readily accessable to the patient allowing the patient to attach the adaptor and external support systems to the access device for self-treatment.

Although the invention has been described with regard to certain embodiments which constitutes the best modes presently known in the invention, it should be understood that various changes and modifications as would be obvious to one having ordinary skill in the art may be made without departing from the scope of the invention which is defined solely by the appended claims.

What is claimed:

1. In combination a device to provide access to a fluid-containing internal region of a living body, a plug and an adaptor;
   said device comprising an access tube providing a first passageway for communication with the internal region and means to anchor said tube in the living body, said access tube having an outer end which is proportioned to extend above the skin when said device is anchored in the living body;
   said plug being proportioned to be received in said access tube and including an inner sealing member which blocks said first passageway and an outer portion which provide a surrounding vacant region within said first passageway, whereby surfaces of said access tube outward of said sealing member can be washed by injecting a cleaning solution into said vacant region when said plug is blocking said first passageway;
   said adaptor comprising a tubular section providing a second passageway for alignment with said first passageway and a chamber portion for receiving said plug when it is withdrawn from said access tube, connecting means for joining one end of said adaptor to said outer end of said access tube, and side passageway means in communication with said second passageway and located between said one end of said adaptor and said chamber portion through which fluid can flow when said plug is withdrawn from said first passageway and located in said chamber portion.

2. A combination according to claim 1 wherein said outer portion of said plug has a center channel and opening means interconnecting said center channel and said vacant region, whereby surfaces of said access tube and said plug can be washed by injecting a cleaning solution into said center channel when said plug is blocking said first passageway.

3. A combination according to claim 1 wherein an extractor is also provided which includes means for linking to said plug for withdrawing said linked plug to said chamber portion.

4. A combination according to claim 3 wherein said adaptor has an open end on the opposite side of said chamber portion from said one end, and said extractor has an end portion insertable through said adaptor, and wherein said linking means is carried by said extractor end portion.

5. A combination according to claim 4 wherein said linking means include an outwardly displaceable ball and said plug includes a groove which is located to receive said ball.

6. A combination in accordance with claim 1 wherein a cap is provided for sealing said exposed end of said blood access device.

7. A combination according to claim 1 wherein said access device includes a tubular conduit insertable in a living blood vessel and from which said access tube extends.

8. An access device according to claim 1 including means to anchor said access tube to a bone.

9. A combination in accordance with claim 8 wherein said anchor means is a sleeve around said access tube having an inner end attachable to bone tissue.

10. A combination in accordance with claim 9 wherein said inner end of said sleeve has a porous surface.

11. In combination a device to provide access to the peritoneal cavity of a living body, a plug and an adaptor;
   said device comprising a rigid access tube having an inner end and an outer end and providing a first passageway, means at said inner end to anchor said device to a rib bone of the living body, said outer end being proportioned to extend above the skin when said rigid tube is anchored to the bone, and a flexible tube extending from said inner end adapted to extend to the peritoneal cavity when said rigid tube is anchored to the bone and communicate the peritoneal cavity to said first passageway;
   said plug being proportioned to be received in said rigid access tube;
   said adaptor comprising a tubular section providing a second passageway for alignment with said first passageway and a chamber portion for receiving said plug when it is withdrawn from said access tube, connecting means for joining one end of said adaptor to said outer end of said access tube, and side passageway-defining means in communication with said second passageway and located between said one end of said adaptor and said chamber portion through which fluid can flow when said plug is withdrawn from said first passageway and located in said chamber portion.

12. A combination according to claim 11 wherein an extractor is also provided which includes means for linking to said plug for withdrawing said linked plug to said chamber.

13. A combination according to claim 12 wherein said adaptor has an open end on the opposite side of said chamber from said one end, and said extractor has an end portion insertable through said adaptor, and wherein said linking means is carried by said extractor end portion.

14. A combination according to claim 13 wherein said linking means include an outwardly displaceable ball and said plug includes a groove which is located to receive said ball.

15. A combination in accordance with claim 11 wherein said plug has an inner sealing member and an outer portion proportioned to provide a surrounding vacant region within said first passageway.

16. A combination in accordance with claim 12 wherein said outer portion of said plug has a center channel and opening means interconnecting said center channel and said vacant region.

17. The combination in accordance with claim 11 wherein said anchor means is a sleeve around said inner end of said access tube, said sleeve having an inner end attachable to rib bone tissue around an opening formed through the rib bone to receive said flexible tubing therethrough.

18. The combination in accordance with claim 17 wherein said inner end of said sleeve has a porous surface to promote bone ingrowth.

19. The combination in accordance with claim 11 wherein said flexible tube has a cuff for suturing to an opening surgically formed in the wall of the peritoneal cavity.

20. In combination, a device to provide access to an internal region of a living body, a plug and an adaptor;

said device comprising an access tube providing a first passageway insertable into a living body for communication with a region containing body fluids and means to anchor said tube in said body, said access tube having an exposed end which is proportioned to extend above the skin when said access means is anchored in a living body;

said plug being proportioned to be received in said access tube and to block fluid flow through said first passageway, said adaptor comprising a tubular section having means at one end for interconnection with said exposed end of said access tube, a chamber portion, an open end on the opposite side of said chamber portion from said one end, a second passageway for alignment with said first passageway, and side passageway-defining means in communication with said second passageway and located between said one end and said chamber portion, and extractor means for withdrawing said linked plug from said access tube to said chamber portion to establish communication between the fluid-containing region and said side passageway-defining means, said extractor means having an end portion insertable through said open end of said adaptor, said end portion having an outwardly displaceable ball and said plug having a groove which is located to receive said ball thereby linking said extractor means to said plug.

* * * * *